United States Patent [19]

Hitzman

[11] 4,096,073

[45] Jun. 20, 1978

[54] MICROBIAL VISCOSIFIERS

[75] Inventor: Donald O. Hitzman, Bartlesville, Okla.

[73] Assignee: Phillips Petroleum Company, Bartlesville, Okla.

[21] Appl. No.: 591,969

[22] Filed: Jun. 30, 1975

[51] Int. Cl.² .............................................. C09K 3/00
[52] U.S. Cl. .............................. 252/8.55 D; 166/273; 195/31 P; 531/1
[58] Field of Search ................... 252/8.55 D, 316; 260/209 R; 195/31 P; 166/273, 274, 275

[56] References Cited

U.S. PATENT DOCUMENTS

| | | | |
|---|---|---|---|
| 3,382,229 | 5/1968 | Patton et al. | 260/209 P |
| 3,632,570 | 1/1972 | Gill | 260/209 R |
| 3,729,460 | 4/1973 | Patton | 252/8.55 D |
| 3,801,502 | 4/1974 | Hitzman | 252/8.55 D |

*Primary Examiner*—Benjamin R. Padgett
*Assistant Examiner*—Josephine L. Barr

[57] ABSTRACT

A method of producing microbial viscosifiers, for use in waterfloods, for instance, which involves mixing fermentation suspensions comprising Gram-negative cells with a base to raise the pH of the resulting solution above 7.

7 Claims, No Drawings

MICROBIAL VISCOSIFIERS

This invention pertains to the production of microbial viscosifiers.

BACKGROUND OF THE INVENTION

In one of its more specific aspects, this invention pertains to the conversion of fermenter effluents into materials suitable as viscosifiers for such things as waterflood oil recovery fluids.

The preparation of thickening agents for use in preparing viscous waterflooding solutions from heteropolysaccharides is well known. The heteropolysaccharides are produced by bacterial action upon a variety of carbohydrate substances. Usually the fermenter liquor as recovered from the fermenter requires some treatment to produce solutions or solids useful for increasing the viscosity of fluids, such as injection water, employed in secondary oil recovery.

SUMMARY OF THE INVENTION

The present invention provides a simple and inexpensive method of increasing the viscosity of fermenter suspensions, comprising predominantly Gram-negative microbial cells themselves, over a wide range of values.

According to the present invention there is provided a method for treating a fermentation suspension comprising Gram-negative cells to produce microbial viscosifiers which comprises contacting the suspension with a base to increase the pH of the resulting solution.

DESCRIPTION OF THE PREFERRED EMBODIMENTS

In general, the method of this invention involves treating cultures of hydrocarbon, carbohydrate or methanol-grown cells from the fermenter with an alkali to increase the pH and the viscosity of the fermenter effluent and to produce a substance useful for increasing the viscosity of aqueous fluids employed in secondary oil recovery.

The fermenter effluent, to which the method of this invention is applicable is one wherein Gram-negative bacterial cells are present.

The method of this invention employs any base capable of raising the pH of the fermenter effluent. Preferably, an alkali metal hydroxide such as NaOH and KOH is employed, although $NH_4OH$ and other alkalis can be employed. The base is added to the fermentation effluent in any convenient manner and at any strength until the resulting liquor has a pH greater than 7, and preferably a pH between 9 and 12, more preferably 9 and 10. Values greater than 12 will usually not be employed. Upon the addition of the base the viscosity of the mixture increases. Intermittent dilution with water or an aqueous solution can be made, before, during, or after the addition of the base in order to facilitate mixing of the effluent and alkali. After the desired pH is attained, further dilution can be made until the mixture attains the desired viscosity. Biocides can also be added during the period of pH adjustment, either with the water or independently thereof.

In certain instances, the viscosity of the solution will continue to increase for a time after the desired pH is attained. Accordingly, viscosity adjustment of the mixture can be made for a period after the pH adjustment has been accomplished, during which period the mixture can be considered as aging. The aging is preferably conducted at a temperature somewhat above room temperature, although the aging can be carried out at 50° to 212° F, preferably 80° to 150° F.

After an aging period of about 4 weeks or less, both the viscosity and the pH of the solution will begin to decrease. Accordingly, then, there is an optimum period of time for aging to achieve maximum viscosity. Generally, aging periods longer than 4 weeks are not employed. Depending on the temperature, the time of aging will generally be at least 5 minutes to allow the alkali to produce the viscosifying properties before the solution is used. Generally a time of 1 day to 4 weeks, preferably 1-3 days will be used. In waterflood applications the material can be injected into the ground where the viscosity will continue to increase.

In applications using the invention, fermenter effluent can be employed, as such, or it can be evaporated to dryness or centrifuged or subjected to any conventional liquid-solid separation step to recover a solid cellular material which can be treated with a base in accordance with this invention to produce a viscosifier. By treating the total fermenter effluent, the water required, if the product is to be used as an injection fluid, is already present. Similarly when this viscosifier is used in other applications such as suspending coal fines for transmission through pipe lines, further diluents may not be necessary.

The alkali treated effluent is referred to herein as a solution. Although it may contain some material in the form of a suspension, probably a colloidal suspension, it has the general appearance of a solution, and hence the term solution appears to best describe this material.

EXAMPLE I

The method of this invention is illustrated by the following example. A fermenter effluent was produced as follows: A continuous fermentation was conducted at $39 \pm 1°$ C in a 7 liter fermenter with the organism *Psuedomonas Methanica* and methanol as the principal source of carbon and energy (nutrient). The medium composition was the following:

| Recipe | |
|---|---|
| Medium Composition | |
| $H_3PO_4$ (85%) ml/l | 2 |
| KCl, g/l | 1.0 |
| $MgSO_4 \cdot 7H_2O$, g/l | 1.5 |
| $CaCl_2 \cdot 2H_2O$, g/l | 0.2 |
| NaCl, g/l | 0.1 |
| Trace Mineral Solution, ml/l | 5 |
| Trace Mineral Solution Recipe | |
| $CuSO_4 \cdot 5H_2O$, g/l | 0.06 |
| KI, g/l | 0.08 |
| $MnSO_4 \cdot H_2O$, g/l | 0.30 |
| $H_3BO_3$, g/l | 0.02 |
| $ZnSO_4 \cdot 7H_2O$, g/l | 2.0 |
| $FeCl_3 \cdot 6H_2O$, g/l | 4.8 |
| $Na_2MoO_4 \cdot 2H_2O$, g/l | 0.2 |
| $H_2SO_4$ (to remove precipitates in trace mineral solution), ml/l | 3 |

The pH of the medium (3.5 l) was adjusted to 4.5 with $NH_3$ and the fermenter and medium sterilized for 30 minutes at 121° C and 15 psig. After cooling to 40° C the sterile trace mineral solution (17.5 ml) and filtered methanol (17.5 ml) was added and pH was adjusted to 6.5 with $NH_4OH$. The inoculum (500 ml) was there added to start fermentation. The fermentation run was carried out for 5 days during which time the feed rate of medium (containing 8% by wt methanol) was gradually increased from 300 to 500 ml/hr. The oxygen addition rate was also increased gradually from 6 l/min of air to a mixture of 5 l/min of air and 1 l/min of pure oxygen. Ammonium hydroxide was also added as required to maintain the pH at 6.5 and to serve as a source of nitrogen for the microorganisms. A portion of the entire fermenter effluent, including as the predominant constituent Gram-negative cells, was treated with 0.32 weight percent (based on cell content) sodium hydroxide to adjust the pH, two parts by volume of tap water being added after 24 hrs. to adjust the viscosity. Aging was conducted at 120° F. The results were as follows:

Table I

| Time | pH | Viscosity* |
|---|---|---|
| Initial |  |  |
| After Alkali Addn. | 9.5 | 6.4 |
| 24 Hours | 9.0 | 21.7 |
| 72 Hours | 10.5 | 14.7 |
| 2 Weeks | 8.1 | 12.8 |
| 3 Weeks | 7.9 | 6.4 |
| 4½ Weeks | 8.2 | 5.8 |

*Measured at 6 rpm on Brookfield LVT with UL attachment at 120° F.

It will be noticed that after the solution attained the desired viscosity and was aged, both the pH and the viscosity of the solution tended to decrease. Hence, aging is conducted to a desired or preselected pH or viscosity, or both, at which point the solution is ready for use as a viscosifier.

EXAMPLE II

The effect of sodium hydroxide on the viscosity of aqueous suspensions of Gram-negative cells and Gram-positive cells was investigated. The cultures were grown in an agitated medium containing 3 grams of yeast extract, 3 grams of malt extract, 5 grams of peptone, and 10 grams of glucose per liter of water, and Gram stains were made to show purity and Gram stain characteristics. The cultures grown were then centrifuged, and the packed cells were washed, recentrifuged, and then suspended in tap water so as to give the same cell density in each instance. To the test tubes containing the cell suspensions was added sufficient 1 N sodium hydroxide to raise the pH to 10. The contents of each tube were mixed and then allowed to stand for 5 minutes, after which the test tube was tipped. If the contents of the test tube had not substantially increased in viscosity, the mixture would pour, but if the viscosity increased substantially, a gel was formed which would not pour. The following table shows the effect of the sodium hydroxide on the suspensions of Gram negative ($g^-$) or Gram-positive ($g^+$) cells.

Table II

| Culture | $g^-$ or $g^+$ | Result of NaOH Addition |
|---|---|---|
| Serratia marscens | $g^-$ | Gel |
| Pseudomonas species PS1 | $g^-$ | Gel |

Table II-continued

| Culture | $g^-$ or $g^+$ | Result of NaOH Addition |
|---|---|---|
| Arthobacter species H010 | $g^-$ | Gel |
| Pseudomonas strain BA623 | $g^-$ | Gel |
| Bacillus megatherium ATCC 10778 | $g^+$ | No change observed |
| Bacillus subtilus | $g^+$ | No change observed |
| Candida lipolytica | $g^+$ | No change observed |
| Endomyces fibriliger ATCC 9947 | $g^+$ | No change observed |
| Hansenula anomala | $g^+$ | No change observed |

Thus, after addition of the sodium hydroxide the viscosity of those suspensions containing the Gram-negative cells increased to such an extent that gel formation occurred whereas there was no observed increase in viscosity of those suspensions containing the Gram-positive cells. While the invention is applicable to any Gram-negative cells including Xanthomonas which produces extracellular gums, the invention is particularly applicable to use with Gram-negative cells which produce no extracellular material such as the four listed above.

EXAMPLE III

Xanthomonas Culture Growth

A lyophilized culture of *Xanthomonas campestris* NRRL B 1459 was received from Northern Regional Research Laboratories of the U.S. Dept. of Agriculture. The culture was grown in a nutrient broth and streaked on plates to determine purity. Gram stains showed the culture was pure. Transfers were made to YM medium in flasks. Composition of the YM medium was as follows:

|  | g/l |
|---|---|
| Yeast extract | 3 |
| Malt extract | 3 |
| Peptone | 5 |
| Dextrose | 10 |
| Distilled water | 1000 ml |

The Xanthomonas culture was a Gram negative small rod. The *Xanthomonas Campestris* B 1459 was inoculated into the YM medium (500 cc medium/1 l. flask) and shaken at room temperature on a rotary shaker. After 5 days abundant growth had occurred and the culture medium had a viscous appearance. The contents of this flask were used to prepare the test solutions for viscosity measurements. The contents of the flask was used in the following scheme with viscosity measurements being made with a Brookfield Synchro-lectric Viscometer Model C at room temperature. The viscosity was measured at 0.6 RPM allowing 30 min. to reach equilibrium. Aqueous sodium hydroxide (10 N) was used to increase the pH in the runs indicated.

Table III

| Culture *Xanthomonas Campestris* B 1459 effluent containing cells and extracellular gum | pH | Brookfield Viscosity 0.6 RPM Room Temp. Viscosity |
|---|---|---|
| Sample |  |  |
| 1   As received from flask, | 6.85 | 35.5 |
| 2   Sample 1 treated with sodium hydroxide, | 9.1 | 36.5 |
| 3   Supernatant liquid from Sample 1 centrifuged to remove cells | 6.95 | 36.0 |
| 4   Sample 3 treated with sodium hydroxide | 9.1 | 33.5 |
| 5   Cells removed from sample 1 by centrifuge and washed to remove gums and then resuspended in distilled water to original volume. | 6.85 | 1.5 |

Table III-continued

| | | pH | Viscosity |
|---|---|---|---|
| 6 | Sample 5 cells treated with sodium hydroxide | 9.1 | 30.0 |

Supernatant liquid from the centrifuged sample (Sample 3) was treated with acetone (100 cc supernatant + 200 cc acetone) which caused gum precipitation. The gum was removed by twisting on a spatula and freeing from acetone. The isolated gum was then resuspended in 100 cc of deionized water and viscosity measured.

| Sample | | pH | Viscosity |
|---|---|---|---|
| 7 | Isolated gum solution. | 6.95 | 135 |
| 8 | Sample 7 treated with sodium hydroxide | 9.1 | 122 |

The response of Gram positive cells was measured by taking cell effluent from a fermenter Run composed of Gram positive rods. The cells were recovered by centrifugation and resuspended in distilled water. The sample was divided and the pH increased in one of the solutions by addition of sodium hydroxide.

| *Bacillus* gram positive cells | | pH | Brookfield Viscometer 6 RPM Viscosity |
|---|---|---|---|
| Sample | | | |
| 9 | Cells centrifuged and resuspended in distilled water | 6.8 | 2.5 |
| 10 | Sample 9 treated with hydroxide | 9.1 | 2.5 |

Also tested were other Gram-positive cells (*Hansenula* species Y 5939). These cells were treated the same way as above.

| *Hansenula* gram positive cells | | pH | Brookfield 6 RPM Viscosity |
|---|---|---|---|
| Sample | | | |
| 11 | Cells centrifuged and resuspended in distilled water | 4.0 | 6. |
| 12 | Sample 11 treated with hydroxide | 9.1 | 3.5 |

These data demonstrate that these gram positive cells show no increase in viscosity when the pH is raised and that it is the gram negative cells, not the gum, which is responsible for the increase in viscosity from adding a base to fermenter effluent containing gram negative cells.

What is claimed is:

1. A method of producing microbial viscosifiers which comprises:
   (a) contacting a fermenter effluent consisting essentially of gram-negative cells of a type which produce no extracellular material as a solid constituent with a base to raise the pH to a value within the range of 9 to 12; and
   (b) aging said thus contacted material containing said base at a temperature of about 50°-212° F for a period of at least 5 minutes to increase the viscosity thereof.

2. A method according to claim 1 wherein said pH is within the range of 9 to 10.

3. A method according to claim 1 wherein said base is sodium hydroxide.

4. A method according to claim 1 wherein said cells are selected from the genus Serratia, the genus Pseudomonas, or the genus Arthobacter.

5. A method according to claim 1 wherein said cells are produced in a fermentation wherein the principal source of carbon and energy is selected from the group consisting of hydrocarbons, carbohydrates, and methanol.

6. A method according to claim 1 wherein said aging period is 1-3 days.

7. A method of producing microbial viscosifiers which comprises:
   (a) contacting a solid constituent consisting essentially of gram-negative cells provided by separating out extracellular material from a fermenter effluent to leave only said cells with a base to raise the pH to a value within the range of 9 to 12; and
   (b) aging the thus contacted material containing said base at a temperature of about 50°-212° F for a period of at least 5 minutes to increase the viscosity thereof.

* * * * *